US007427591B2

(12) United States Patent
Ploegh et al.

(10) Patent No.: US 7,427,591 B2
(45) Date of Patent: Sep. 23, 2008

(54) SUPPRESSION OF IMMUNE RESPONSE VIA INHIBITION OF CATHEPSIN S

(75) Inventors: Hidde L. Ploegh, Brookline, MA (US); Harold A. Chapman, Newton, MA (US); Richard J. Riese, Brookline, MA (US); Paula R. Bryant, Cambridge, MA (US); Matthew S. Bogyo, San Francisco, CA (US)

(73) Assignees: Massachusetts Institute of Technology, Cambridge, MA (US); Brigham and Women's Hospital, Boston, MA (US)

( * ) Notice: Subject to any disclaimer, the term of this patent is extended or adjusted under 35 U.S.C. 154(b) by 338 days.

(21) Appl. No.: 10/913,045

(22) Filed: Aug. 5, 2004

(65) Prior Publication Data

US 2005/0095248 A1    May 5, 2005

Related U.S. Application Data

(63) Continuation of application No. 10/641,872, filed on Aug. 14, 2003, which is a continuation of application No. 10/126,223, filed on Apr. 19, 2002, which is a continuation of application No. 09/155,956, filed as application No. PCT/US97/06865 on Apr. 22, 1997, now Pat. No. 6,608,030.

(60) Provisional application No. 60/018,100, filed on Apr. 22, 1996.

(51) Int. Cl.
*A61K 38/00* (2006.01)
*A61K 38/02* (2006.01)

(52) U.S. Cl. .............................. 514/2; 514/885; 424/810

(58) Field of Classification Search .................... 514/13, 514/14, 15, 16, 17, 18, 19
See application file for complete search history.

(56) References Cited

U.S. PATENT DOCUMENTS

| 5,422,359 A | 6/1995 | Ando et al. |
| 5,501,969 A | 3/1996 | Hastings et al. |
| 5,510,333 A | 4/1996 | Angelastro et al. |
| 5,559,028 A | 9/1996 | Humpreys |

FOREIGN PATENT DOCUMENTS

| WO | WO-94/04557 | 3/1994 |
| WO | WO-95/23222 | 8/1995 |
| WO | WO-96/30353 | 10/1996 |

OTHER PUBLICATIONS

Ahmed N.K. et al. "Peptidyl Fluoromethyl Ketones as Inhibitors of Cathepsin B: Implication for Treatment of Rheumatoid Arthritis", Biochemical Pharmacology 44(6):1201-1207 (1992).
Bromme, D. et al. "Peptidyl vinyl sulphones: a new class of potent and selective cysteine protease inhibitors", Biochem J. 315:85-89 (1996).
Bromme, D. et al. "N-Peptidyl-o-carbamoyl amino acid hydroxamates: Irreversible inhibitors for the study of the S2' specificity of cysteine proteinases", FEBS 12414 322(3):211-214 (1993).
Bromme, D. et al. "Potent Inactivitation of Cathepsins S and L by Peptidyl (Acyloxy)methyl Ketones", Biol. Chem. Hoppe-Seyler 375:343-347 (1994).
Bromme, D. et al. "The Specificity of Bovine Spleen Cathepsin S: A comparison with rat liver cathepsins L and B", Biochem J. 264:475-481 (1989).
Carmona, E. et al. "Potency and Selectivity of the Cathepsin L Propeptide as an Inhibitor of Cysteine Protease", Biochemistry 35:8149-8157 (1996).
Demuth, H.U., et al. "N-peptidyl, O-acyl hydroxamates: comparison of the selective inhibition of serine and cystein proteinases", Biochimica et Biophysica Acta, 1295:179-186 (1996).
Gour-Salin, B.J. "E-64 Analogs as Inhibitors of Cathepsin L and Cathepsin S: Importance of the S2-P2 Interactions for Potency and Selectivity", Bioorganic Chemistry 22:227-241 (1994).
Hanzlik et al., "Vinylogous Amino Acid Esters: A New Class of Inactivators of Thiol Proteases", Journal of Medicinal Chemistry, 27(6):711-712 (1984).
Hughes, E.A. et al. "The Protease Inhibitor, N-Acetyl-L-Leucyl-L-Leucyl- L-Norleucinal, Decreases the Pool of Major Histocompatibility Complex Class I-binding Peptides and Inhibits Peptide Trimming in the Endoplasmic Reticulum", J. Exp. Med. 183:1569-1578 (1996).
Kirschke, H. et al. "Cathepsin S and Related Lysosomal Endopeptidases" Cysteine Peptidases Academic Press, Inc. 34:500-511 (1994).
Valderrama, et al., J. Neurological Sciences, 82 (1-3): 133-143 (1987).
McDonald et al., Arch. Biochem. Biophys., 305 (1): 1-8 (1993).
Takei et al., Transplantation, 50 (1): 14-20 (1990).
Eisenbarth et al., New England Journal of Medicine, 298 (2): 93 (1978).
Lenarcic et al., "Pig leukocyte cysteine proteinase inhibitor (PLCPI), a new memeber of the stefin family", FEBS 13443 336(2):289-292 (1993).
Morton, P. et al. "Delivery of Nascent MHC Class II-Invariant Chain Complexes to Lysosomal Compartments and Proteolysis of Invariant Chain by Cysteine Proteases Precedes Peptide Binding in B-Lymphoblastoid Cells", The Journal of Immunology 154:137-150 (1995).

(Continued)

*Primary Examiner*—David A Saunders
*Assistant Examiner*—F. Pierre VanderVegt
(74) *Attorney, Agent, or Firm*—Ropes & Gray LLP

(57) ABSTRACT

Methods and products for suppressing a class II MHC-restricted immune response in a mammal, or in mammalian cells, are described. The methods depend upon inhibiting invariant chain proteolysis by cathepsin S from class II MHC/invariant chain complexes, thereby reducing the competency of class II MHC molecules for binding antigenic peptides, reducing presentation of antigenic peptides by class II MHC molecules, and suppressing immune responses. The methods may be employed in the treatment of autoimmune diseases, allergic responses, and organ or tissue graft rejection. Pharmaceutical and therapeutic compositions which are peptide based inhibitors of cathepsin S are also described.

17 Claims, No Drawings

OTHER PUBLICATIONS

Okamoto, K. et al. "The Characterization of the Inhibition of Mature Cysteine Proteases By Their Proregions", J. of Cellular Biochemistry Suppl. 0(1913):254 (1995).

Palmer, J.T., et al. "Vinyl Sulfones as Mechanism-Based Cysteine Protease Inhibitors", J.Med.Chem. 38:3193-3196 (1995).

Petanceska, S. et al. "Expression of Rat Cathepsin S in Phagocytic Cells", The Journal of Biological Chemistry 271 (8):4403-4409 (1996).

Pohl, J. et al. "Chromophoric and Fluorophoric Peptide Substrates Cleaved through the Dipeptidyl Carboxypeptidase Activity of Cathepsin B", Analytical Biochemistry 165:96-101 (1987).

Riese, R.J., et al. "Essential Role for Cathepsin S in MHC Class II-Associated Invariant Chain Processing and Peptide Loading", Immunity 4:357-366 (1996).

Shaw, E. et al. "The affinity-labelling of cathepsin S with peptidyl diazomethyl ketones: Comparison with the inhibition of cathespin L and calpain", FEBS 13268 334(3):340-342 (1993).

Shi, G.P. et al. "Human Cathepsin S: Chromosomal Localization, Gene Structure, and Tissue Distribution", The Journal of Biological Chemistry 269(15):11530-11536 (1994).

Turk, V., et al. "Human Cysteine Proteinases and Their Inhibitors, Stefins and Cystatins" in Biological Functions of Proteases and Inhibitors, N. Katunuma et al., eds. Japanese Scientific Press, Tokyo Japan, Chap. 4:47-59 (1994).

SUPPRESSION OF IMMUNE RESPONSE VIA INHIBITION OF CATHEPSIN S

RELATED APPLICATIONS

This is a continuation of prior application U.S. Ser. No. 10/641,872, filed on Aug. 12, 2003, which is a continuation of U.S. Ser. No. 10/126,223, filed on Apr. 19, 2002, which is a continuation of U.S. Ser. No. 09/155,956, filed May 19, 1999, now U.S. Pat. No. 6,608,030, which claims benefit of priority to International Application Serial No. PCT/US97/06865, filed on Apr. 22, 1997; which claims priority to U.S. provisional application Ser. No. 60/018,100, filed on Apr. 22, 1996, the entire disclosures of which are incorporated by reference herein.

GOVERNMENT SUPPORT

The present invention was supported, in part, by grant 5-R01-A134893 from the National Institutes of Health. Therefore, the government may have certain rights in the invention.

FIELD OF THE INVENTION

The present invention relates to novel methods and products directed to immunosuppression via the inhibition of cathepsin S. The methods and products may by employed for the treatment of autoimmune diseases, as well as reducing the competency of class II MHC molecules for binding antigenic peptides.

BACKGROUND OF THE INVENTION

Class II MHC (major histocompatibility complex) cellular proteins (αβ heterodimers) associate early during biosynthesis with a type II membrane polypeptide, the invariant chain (Ii), to form class II MHC/invariant chain complexes (αβ Ii). It has been reported that the invariant chain associates with class II MHC molecules via direct interaction of residues 81-104 of its lumenal domain, designated class II associated invariant chain peptides (CLIP), with the antigen binding groove of class II MHC.

The invariant chain contains a signal in its cytoplasmic tail which delivers the class II MHC/invariant chain complexes to intracellular endocytic compartments, where the class II MHC molecules encounter and bind antigenic peptides. A prerequisite for antigenic peptide loading of class II MHC molecules is the proteolytic destruction of the invariant chain from the class II MHC/invariant chain complexes. Identification of the specific key protease responsible for this proteolysis has not previously been reported. Proteolysis of the invariant chain allows the antigenic peptides to bind to the class II MHC molecules to form class II MHC/antigenic peptide complexes.

The antigenic peptides in these complexes are then deposited on the cell surface for recognition by CD4+ T cells. These T cells are involved in the production of cytokines and thus help orchestrate an immune response, culminating in the appropriate production of antibodies. On occasion, CD4+ cells are activated inappropriately and are believed to contribute to the pathology of autoimmune disease.

SUMMARY OF THE INVENTION

In one aspect, the present invention provides methods for inhibiting invariant chain proteolysis from class II MHC/invariant chain complexes, reducing the competency of class II MHC molecules for binding antigenic peptides, and reducing the presentation of antigenic peptide by class II MHC molecules, by administering to a mammalian cell, in vivo or in vitro, an amount of an inhibitor of cathepsin S effective to substantially inhibit proteolysis of invariant chain by cathepsin S.

In another aspect, the present invention provides methods for modulating class II MHC-restricted immune responses. Such immune responses are essential to autoimmune diseases, allergic reactions, and allogeneic tissue rejections. Therefore, the present invention also provides methods for suppressing class II MHC-restricted immune responses and, in particular, autoimmune, allergic, and allogeneic immune responses, by administering to a mammal (e.g., a human patient) a therapeutically effective amount of an inhibitor of cathepsin S to reduce the presentation of antigenic peptides by class II MHC molecules and, thereby, provide a degree of relief from these conditions. In preferred embodiments, methods are provided for the treatment of autoimmune diseases including juvenile onset diabetes (insulin dependent), multiple sclerosis, pemphigus vulgaris, Graves' disease, myasthenia gravis, systemic lupus erythematosus, rheumatoid arthritis and Hashimoto's thyroiditis. In other preferred embodiments, methods are provided for treating allergic responses, including asthma, and for treating allogeneic immune response, including those which result from organ transplants, including kidney, lung, liver, and heart transplants, or from skin or other tissue grafts.

The inhibitors of cathepsin S may be any molecular species which inhibit the transcription of a cathepsin S gene, the processing or translation of a cathepsin S mRNA, or the processing, trafficking or activity of a cathepsin S protein, when administered in vivo or in vitro to a mammalian cell which is otherwise competent to express active cathepsin S. In particular, inhibitors may be repressors, or antisense sequences, or competitive and non-competitive inhibitors such as small molecules which structurally mimic the natural substrates of cathepsin S but which are resistant to the proteolytic activity of the enzyme, or antibodies, ribozymes, and the like. Preferably, the inhibitors are cysteine protease inhibitors.

In preferred embodiments, the cathepsin S inhibitors are "selective" inhibitors of cathepsin S which fail to inhibit, or inhibit to a substantially lower degree, at least one of cathepsins K, L, H, O2 and B, and in most preferred embodiments, the inhibitors are "specific" inhibitors of cathepsin S which fail to inhibit, or inhibit to a substantially lower degree, each of cathepsins K, L, H, O2 and B.

In addition, preferred inhibitors include peptide-based inhibitors which mimic a portion of a naturally occurring cathepsin S substrate. Such peptide based inhibitors include peptidyl aldehydes, nitriles, α-ketocarbonyls, halomethyl ketones, diazomethyl ketones, (acyloxy)-methyl ketones, vinyl sulfones, ketomethylsulfonium salts, epoxides, and N-peptidyl-O-acyl-hydroxylamines. Preferred peptide-based inhibitors of cathepsin S also include those based upon the sequences Leu-Leu-Leu, and Leu-Hph, such as Leu-Leu-Leu-vinyl sulfone, N-(carboxybenzyl)-Leu-Leu-Leu-vinyl-sulfone, N-(nitrophenylacetyl)-Leu-Leu-Leu-vinylsulfone, and morpholinurea-Leu-Hph-vinylsulfone phenyl (LHVS).

In another aspect, the present invention provides a new class of peptide-based inhibitors of cathepsin S based upon the newly disclosed preferred chain cleavage site spanning from N-terminally about positions 68-75 to C-terminally about positions 83-90 of the invariant chain sequence. Thus, peptide-based inhibitors of cathepsin S based upon a sequence of 2-20, more preferably 2-10, and most preferably 2-3 consecutive residues from within this site are provided. Particularly preferred are peptide-based inhibitors of cathepsin S based upon the sequences Asn-Leu, Glu-Asn-Leu, Arg-Met, and Leu-Arg-Met (positions 77, 78, and 79; or −3, −2 and −1 relative to the $Lys_{80}$ cleavage point) are preferably used as a basis for choosing or designing a peptide based inhibitor.

Thus, for example, the invention provides novel peptide-based inhibitors such as vinylsulfones compounds including Asn-Leu-vinylsulfone, Arg-Met-vinylsulfone, Leu-Arg-Met-vinylsulfone, and Glu-Asn-Leu-vinylsulfone. Modifications of these peptide vinylsulfones are also included in the invention. For example, carboxybenzyl can be present at the N-terminal end to give the following compounds: N-(carboxybenzyl)-Asn-Leu-vinylsulfone, N-(carboxybenzyl)-Arg Met-vinylsulfone, N-(carboxybenzyl)-Leu-Arg-Met-vinylsulfone, and N-(carboxybenzyl)-Glu-Asn-Leu-vinylsulfone. In an alternative, nitrophenylacetyl is present at the N-terminal end to give the following compounds: N-(nitrophenylacetyl)-Asn-Leu-vinylsulfone, N-(nitrophenylacetyl)-Arg-Met-vinylsulfone, N-(nitrophenylacetyl)-Leu-Arg-Met-vinylsulfone, and N-(nitrophenylacetyl)-Glu-Asn-Leu-vinylsulfone.

The invention is also meant to include other peptide-based inhibitors based on the peptide sequences of the preferred invariant chain cleavage site of cathepsin S, including peptidyl aldehydes, nitriles, α-ketocarbonyls, halomethyl ketones, diazomethyl ketones, (acyloxy)-methyl ketones, vinyl sulfones, ketomethylsulfonium salts, epoxides, and N-peptidyl-O-acyl-hydroxylamines, and those with various other substitutions at the amino terminus as would be known to those skilled in the art.

Other embodiments of the present invention will be apparent to one of ordinary skill in the art from the foregoing and from the Detailed Description and Examples presented below.

DETAILED DESCRIPTION

The present invention is based, in part, upon the discovery that the mammalian cysteine protease cathepsin S is of primary importance in the proteolysis of invariant chain polypeptides complexed to class II MHC αβ heterodimers. In particular, it is herein disclosed that cathepsin S appears to be responsible for the normal cleavage of the invariant chain polypeptide while it is associated in class II MHC/invariant chain complexes and, therefore, that inhibition of cathepsin S inhibits the proteolysis of invariant chain from class II MHC/invariant chain complexes and inhibits the formation of class II MHC/CLIP complexes. Consequently, because class II MHC molecules remain associated in class II MHC/invariant chain complexes, inhibition of cathepsin S reduces the competency of class II MHC molecules for binding antigenic peptides and reduces the presentation of antigenic peptides by class II MHC molecules.

Therefore, in one aspect, the present invention provides for methods for inhibiting invariant chain proteolysis from class II MHC/invariant chain complexes, reducing the competency of class II MHC molecules for binding antigenic peptides, and reducing the presentation of antigenic peptide by class II MHC molecules, by administering to a mammalian cell, in vivo or in vitro, an amount of an inhibitor of cathepsin S effective to substantially inhibit proteolysis of invariant chain by cathepsin S.

In another aspect, because presentation of antigenic peptides complexed with class II MHC molecules is essential to immune responses which are class II MHC-restricted, the present invention also provides methods for modulating class II MHC-restricted immune responses. Such immune responses are essential to autoimmune diseases, allergic reactions, and allogeneic tissue rejections. Therefore, the present invention also provides methods for suppressing class II MHC-restricted immune responses and, in particular, autoimmune, allergic, and allogeneic immune responses, by administering to a mammal (e.g., a human patient) a therapeutically effective amount of an inhibitor of cathepsin S to reduce the presentation of antigenic peptides by class II MHC molecules and, thereby, provide a degree of relief from these conditions.

The present invention is further based, in part, upon the discovery that cathepsin S normally acts on class II MHC/invariant chain complexes at one of two, nearly adjacent, preferred invariant chain cleavage sites. In particular, it is herein disclosed that human cathepsin S normally cleaves the invariant chain at the peptide bonds C-terminal to residues $Arg_{78}$ and $Lys_{80}$ of the invariant chain sequence (SEQ ID NO: 1).

Therefore, in another aspect, the present invention provides for a new class of peptidebased inhibitors of cathepsin S. These peptide-based cathepsin S inhibitors are based upon the amino acid residue sequences immediately surrounding the cleavage sites which are recognized, bound, and cleaved by cathepsin S (e.g., residues 68-90, or 73-85 of SEQ ID NO: 1). The peptide-based cathepsin S inhibitors may be actual peptides or, more preferably, peptide derivatives or modified peptides which retain sufficient structural similarity to the natural substrate to retain binding activity, but which may be structurally modified to render them noncompetitive inhibitors or to otherwise enhance their stability.

Preferred embodiments and exemplifications of the present invention are described in detail below.

I. Definitions

In order to more clearly and concisely describe and disclose the subject matter of the claimed invention, the following definitions are provided for specific terms used in the specification and appended claims.

As used herein; an "inhibitor of cathepsin S" is any molecular species which inhibits the transcription of a cathepsin S gene, the processing or translation of a cathepsin S mRNA, or the processing, trafficking or activity of a cathepsin S protein, when administered in vivo or in vitro to a mammalian cell which is otherwise competent to express active cathepsin S. Thus, for example, the term "inhibitor of cathepsin S" embraces a repressor which inhibits induction and/or transcription of the cathepsin S gene, or an antisense sequence which selectively binds to cathepsin S DNA or mRNA sequences and which inhibits the transcription or translation of the cathepsin S sequences. Similarly, the term "inhibitor of cathepsin S" includes competitive and non-competitive inhibitors of the activity of the cathepsin S protein, such as small molecules which structurally mimic the natural substrates of cathepsin S but which are resistant to the proteolytic activity of the enzyme. Although an inhibitor of cathepsin S may have some degree of inhibitory activity for other genes or proteins which are structurally or functionally related, the term "inhibitor of cathepsin S" is not intended to embrace non-selective suppressors of all gene expression or protein synthesis, or general toxins (e.g., transcription blockers such as actinomycin D, and (α-amanitin; protein synthesis inhibitors such as puromycin, cycloheximide, and diptheria toxin).

As used herein, a "cysteine protease inhibitor" is any molecular species which inhibits one or more of the mammalian enzymes known as cysteine proteases and, in particular, which inhibits cathepsin S. The cysteine proteases, which are also known as thiol or sulfhydryl proteases or proteinases, are proteolytic enzymes with active site cysteine residues which act as nucleophiles during catalysis. Cysteine proteases include papain, calpain I, calpain II, cruzain, and cathepsins S, K, L, H, O2 and B. (Note that cathepsin D is an aspartyl protease.)

As used herein, a "selective inhibitor of cathepsin S" is any molecular species which, as defined above, is an inhibitor of cathepsin S but which fails to inhibit, or inhibits to a substantially lower degree, at least one of cathepsins K, L, H, O2 and B. In preferred embodiments, a selective inhibitor of cathepsin S is employed which has a second order rate constant of inactivation or inhibition for cathepsin S which is at least twice and, more preferably, five times higher than the corresponding rate constant for at least one of cathepsins K, L, H, O2 and B. Most preferably, a selective inhibitor of cathepsin S has a second order rate constant of inactivation for cathepsin S which is at least an order of magnitude or, most preferably, at least two orders of magnitude higher than its inactivation rate constant for at least one of cathepsins K, L, H, 02 and B. As used herein, the term "second order rate constant of inactivation" is intended to mean that quantity as known in the art, and represented as $k_{inact}/K_i$ or as $k_2/K_i$. See, e.g., Brömine et al., *Biol. Chem.* 375:343-347 (1994); Palmer et al., *J. Med. Chem.* 38:3193-3196 (1995); Brömme et al., *Biochem. J.* 315:85-89 (1996).

As used herein, a "specific inhibitor of cathepsin S" is any molecular species which, as defined above is an inhibitor of cathepsin S but which fails to inhibit, or inhibits to a substantially lower degree each of cathepsins K, L, H, O2 and B. In preferred embodiments, a specific inhibitor of cathepsin S is employed which has a second order rate constant of inactivation for cathepsin S which is at least twice and, more preferably, five times higher than the corresponding rate constants for each of cathepsins K, L, H, O2 and B. Most preferably, a specific inhibitor of cathepsin S has a second order rate constant of inactivation for cathepsin S which is at least an order of magnitude or, most preferably, at least two orders of magnitude higher than its second order rate constants for each of cathepsins K, L, H, O2 and B.

As used herein with respect to class II MHC-restricted immune responses, "suppressing" means reducing in degree or severity, or extent or duration, the overt manifestations of the immune response including, for example, reduced binding and presentation of antigenic peptides by class II MHC molecules, reduced activation of T-cells and B-cells, reduced humoral and cell-mediated responses and, as appropriate to the particular immune response, reduced inflammation, congestion, pain, or necrosis. "Suppression" of an immune response does not require complete negation or prevention of any of these manifestations of an immune response, but merely a reduction in degree or severity, or extent or duration, which is of clinical or other practical significance.

As used herein with. respect to inhibitors of cathepsin S, the terms "peptide-based" and "non-peptide-based" do not mean that an inhibitor does, or does not, comprise a peptide or polypeptide, but that the structure of the inhibitor is based upon, or is not based upon, the structure of a polypeptide sequence which binds as a substrate in the active site of cathepsin S.

II. Inhibition of Invariant Chain Proteolysis, Antigen Binding, and Antigen Presentation As noted above, and as evidenced in the examples below, cathepsin S is believed to be important to normal proteolytic processing of the invariant chain. Therefore, in one aspect, the present invention provides methods for inhibiting invariant chain proteolysis from class II MHC/invariant chain complexes in mammalian cells, in vivo or in vitro, by administering an inhibitor of cathepsin S to the cells. As a result of the inhibition of cathepsin S, proteolysis of the invariant chain from class II MHC/invariant chain complexes within the cells is also inhibited.

Furthermore, under normal physiological conditions, inhibition of the proteolysis of the invariant chain inhibits formation of class II MHC/CLIP (also referred to as ($\alpha\beta$-CLIP) complexes. Therefore, as class II MHC/CLIP complexes are more readily loaded with antigenic peptides than class II MHC/invariant chain complexes, the inhibition of cathepsin S and consequent inhibition of MHC/CLIP complex formation reduces the competency of class II MHC molecules for binding antigenic peptides. Therefore, in one aspect, the present invention provides methods for reducing the competency of class II MHC molecules for binding antigenic peptides in mammalian cells, in vivo or in vitro, by administering an inhibitor of cathepsin S to the cells. As a result of inhibition of cathepsin S, proteolysis of the invariant chain is inhibited, formation of class II MHC/CLIP complexes is inhibited, and the competency of the MHC molecules to bind antigenic peptides is reduced.

Similarly, under normal physiological conditions, inhibition of the proteolysis of the invariant chain inhibits the loading and presentation of class II MHC molecules with antigenic peptides. Thus, as class II MEC/CLIP complexes are more readily loaded with antigenic peptides than class II MHC/invariant chain complexes, the inhibition of cathepsin S and consequent inhibition of MHC/CLIP complex formation reduces the loading and presentation of antigenic peptide by class II MHC molecules. Therefore, in one aspect, the present invention provides methods for reducing the presentation of antigenic peptides by class II MHC molecules in mammalian cells, in vivo or in vitro, by administering an inhibitor of cathepsin S to the cells. As a result of inhibition of cathepsin S, proteolysis of the invariant chain is inhibited, formation of class II MHC/CLIP complexes is inhibited, and the loading and presentation of antigenic peptides by class II MHC molecules is reduced.

When employed with mammalian cells in vitro, such methods have utility in preventing the loading of MHC molecules with antigenic peptides and in the production of empty MHC molecules. Empty MHC molecules have utility for subsequent loading and use as analytical, diagnostic and therapeutic agents. Alternatively, by exposing such cells in culture to high concentrations of desired antigenic peptides, or precursors of such peptides, a large proportion of MHC molecules loaded with the desired peptides may be produced. Class II MHC molecules selectively loaded with particular peptides also have utilities in analytical, diagnostic and therapeutic applications.

In these methods, an inhibitor of cathepsin S is administered to, provided to, or contacted with the cells in any manner which allows the inhibitor to enter the cells and inhibit cathepsin S. When employed in vitro, the inhibitors are typically added to the cell culture medium, although microinjection may be employed if desired. When employed in vivo, the inhibitors may be administered as described below in relation to the therapeutic methods.

III. Suppression of Class II MHC-Restricted Immune Responses

As noted above, and as evidenced in the examples below, cathepsin S is believed to be important to important to normal class II MHC-restricted immune responses in mammals Therefore, in one aspect, the present invention provides methods for suppressing class II MHC-restricted immune responses in mammals by administering an inhibitor of cathepsin S to the mammal. As a result of cathepsin S inhibition, the proteolysis of invariant chains, formation of class II MHC/CLIP complexes, and loading and presentation of antigenic peptides are inhibited and, therefore, class II MHC-restricted immune response is suppressed.

In one series of embodiments, the methods are employed to treat mammals, particularly humans, at risk of, or afflicted with, autoimmune disease. By autoimmunity is meant the phenomenon in which the host's immune response is turned against its own constituent parts, resulting in pathology. Many human autoimmune diseases are associated with certain class II MHC-complexes. This association occurs because the structures recognized by T cells, the cells that cause autoimmunity, are complexes comprised of class II MHC molecules and antigenic peptides. Autoimmune disease can result when T cells react with the host's class II MHC molecules when complexed with peptides derived from the host's own gene products. If these class II MHC/antigenic peptide complexes are inhibited from being formed, the autoimmune response is reduced or suppressed. Any autoimmune disease in which class II MHC/antigenic peptide complexes play a role may be treated according to the methods of the present invention. Such autoimmune diseases include, e.g., juvenile onset diabetes (insulin dependent), multiple sclerosis, pemphigus vulgaris, Graves' disease, myasthenia gravis, systemic lupus erythematosus, rheumatoid arthritis and Hashimoto's thyroiditis.

In another series of embodiments, the methods are employed to treat mammals, particularly humans, at risk of, or afflicted with, allergic responses. By "allergic response" is meant the phenomenon in which the host's immune response to a particular antigen is unnecessary or disproportionate, resulting in pathology. Allergies are well known in the art, and the term "allergic response" is used herein in accordance with standard usage in the medical field. Examples of allergies include, but are not limited to, allergies to pollen, "ragweed," shellfish, domestic animals (e.g., cats and dogs), bee venom, and the like. Another particularly contemplated allergic response is that which causes asthma. Allergic responses may occur in part, because T cells recognize particular class II MHC/antigenic peptide complexes. If these class II MHC/antigenic peptide complexes are inhibited from being formed, the allergic response is reduced or suppressed. Any allergic response in which class II MHC/antigenic peptide complexes play a role may be treated according to the methods of the present invention. Although it is not expected that immunosuppression by the methods of the present invention will be a routine prophylactic or therapeutic treatment for common allergies, severe or life-threatening allergic responses, as may arise during asthmatic attacks or anaphylactic shock, may be treated according to these methods.

In another series of embodiments, the methods are employed to treat mammals, particularly humans, which have undergone, or are about to undergo, an organ transplant or tissue graft. In tissue transplantation (e.g., kidney, lung, liver, heart) or skin grafting, when there is a mismatch between the class II MHC genotypes (HLA types) of the donor and recipient; there may be a severe "allogeneic" immune response against the donor tissues which results from the presence of non-self or allogeneic class II MHC molecules presenting antigenic peptides on the surface of donor cells. To the extent that this response is dependent upon the formation of class II MHC/antigenic peptide complexes, inhibition of cathepsin S may suppress this response and mitigate the tissue rejection. An inhibitor of cathepsin S can be used alone or in conjunction with other therapeutic agents, e.g., as an adjunct to cyclosporin A and/or antilymphocyte gamma globulin, to achieve immunosuppression and promote graft survival. Preferably, administration is accomplished by systemic application to the host before and/or after surgery. Alternatively or in addition, perfusion of the donor organ or tissue, either prior or subsequent to transplantation or grafting, may be effective.

In order to minimize the potential for undesired side effects, it is preferred in each of the above-described embodiments that an inhibitor of cathepsin S is chosen which is a selective inhibitor of cathepsin S, a specific inhibitor of cathepsin S, or a highly specific inhibitor of cathepsin S. Thus, for example, it may not be desirable to inhibit, even briefly, all proteases or all cysteine proteases in a cell or an organism because normal protein processing and turnover will be disrupted. To the extent that such incidental inhibition is deleterious or undesired, the use of increasingly more selective cathepsin S inhibitors may be preferred. The use of more selective cathepsin S inhibitors may, for example, allow for the use of higher dosages or more extended treatment periods.

Administration of the inhibitor can be accomplished by any method which allows the inhibitor to reach the target cells, e.g., class II MHC antigen presenting cells. These methods include, e.g., injection, infusion, deposition, implantation, anal or vaginal supposition, oral ingestion, inhalation, topical administration, or any other method of administration where access to the target cells by the inhibitor is obtained. Injections can be, e.g., intravenous, intradermal, subcutaneous, intramuscular or intraperitoneal. For example, the inhibitor can be injected intravenously or intramuscularly for treatment of multiple sclerosis, or can be injected directly into the joints for treatment of arthritic disease, or can be injected directly into the lesions for treatment of pemphigus vulgaris. In certain embodiments, the injections can be given at multiple locations. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Inhalation includes administering the inhibitor with an aerosol in an inhaler, either alone or attached to a carrier that can be absorbed. For systemic administration, it may be preferred that the inhibitor is encapsulated in liposomes. Topical administration can be accomplished with, e.g., ointments, creams or lotions, which are applied topically to the affected area of the skin. In such compositions, the inhibitor can, e.g., be dissolved in a solvent, and then mixed with, e.g., an emulsion or a gelling agent, as are well known to persons ordinarily skilled in the art.

In certain embodiments of the invention, the administration can be designed so as to result in sequential exposures to the inhibitor over some time period, e.g., hours, days, weeks, months or years. This can be accomplished by repeated administrations of the inhibitor by one of the methods described above, or alternatively, by a controlled release delivery system in which the inhibitor is delivered to the mammal over a prolonged period without repeated administrations. By a controlled release delivery system is meant that total release of the inhibitor does not occur immediately upon administration, but rather is delayed for some time period. Release can occur in bursts or it can occur gradually and continuously. Administration of such a system can be, e.g., by long acting oral dosage forms, bolus injections, transdermal patches and subcutaneous implants.

Examples of systems in which release occurs in bursts include, e.g., systems in which the inhibitor is entrapped in liposomes which are encapsulated in a polymer matrix, the liposomes being sensitive to specific stimuli, e.g., temperature, pH, light or a degrading enzyme, and systems in which the inhibitor is encapsulated by an ionically-coated microcapsule with a microcapsule core degrading enzyme. Examples of systems in which release of the inhibitor is gradual and continuous include, e.g., erosional systems in which the inhibitor is contained in a form within a matrix, and diffusional systems in which the inhibitor permeates at a controlled rate, e.g., through a polymer. Such sustained release systems can be, e.g., in the form of pellets or capsules.

The inhibitor can be suspended in a liquid, e.g., in dissolved form or colloidal form. The liquid can be a solvent, partial solvent or nonsolvent. In many cases water or an organic liquid can be used.

The inhibitor is administered to the mammal in a therapeutically effective amount. By therapeutically effective amount is meant that amount which is capable of at least partially preventing, reversing, reducing, decreasing, ameliorating or otherwise suppressing the particular immune response being treated. A therapeutically effective amount can be determined on an individual basis and will be based, at least in part, on consideration of the species of mammal; the mammal's age, sex, size, and health; the inhibitor used; the type of delivery system used; the time of administration relative to the severity of the disease; and whether a single, multiple, or controlled release dose regimen is employed. A therapeutically effective amount can be determined by one of ordinary skill in the art employing such factors and using no more than routine experimentation.

Preferably, the concentration of the inhibitor if administered systematically is at a dose of about 1.0 mg to about 2000 mg for an adult of 70 kg body weight, per day. More preferably, the dose is about 10 mg to about 1000 mg/70 kg/day. Most preferably, the dose is about 100 mg to about 500 mg/70 kg/day. Preferably, the concentration of the inhibitor if applied topically is about 0.1 mg to 500 mg/gm of ointment, more preferably is about 1.0 mg to about 100 mg/gm ointment, and most preferably is about 30 mg to about 70 mg/gm ointment. The specific concentration partially depends upon the particular inhibitor used, as some are more effective than others. The dosage concentration of the inhibitor that is actually administered is dependent at least in part upon the particular immune response being treated, the final concentration of inhibitor that is desired at the site of action, the method of administration, the efficacy of the particular inhibitor, the longevity of the particular inhibitor, and the timing of administration relative to the severity of the disease. Preferably, the dosage form is such that it does not substantially deleteriously affect the mammal. The dosage can be determined by one of ordinary skill in the art employing such factors and using no more than routine experimentation.

III. Inhibitors of Cathepsin S

The present invention employs inhibitors of cathepsin S in a variety of methods, as described above, and also provides for a new class of novel peptide-based cathepsin S inhibitors. Therefore, the present invention provides for the use of an inhibitor of cathepsin S in a medicament, or in a pharmaceutical or therapeutic preparation, for inhibiting invariant chain proteolysis from class II MHC/invariant chain complexes, for reducing the competency of class II MHC molecules for binding antigenic peptides, for reducing presentation of antigenic peptide by class II MHC molecules, for suppressing a class II MHC-restricted immune response, or for treating an autoimmune disease, allergic response, or allogeneic immune response.

The inhibitors of cathepsin S, as used in the methods of the present invention, may be regarded as being prior art inhibitors of cathepsin S, the novel peptide-based inhibitors of cathepsin S disclosed herein, or currently unknown or undisclosed inhibitors of cathepsin S which, for purposes of the present invention, are equivalents to the prior art and presently disclosed inhibitors. Alternatively, and as discussed below, inhibitors of cathepsin S may be regarded broadly as being non-peptide-based inhibitors or peptide-based inhibitors, as defined above.

A. Non-Peptide-Based Inhibitors

Non-peptide-based inhibitors of cathepsin S include repressors, antisense sequences, and non-peptide-based competitive and non-competitive inhibitors.

At present, there are no known repressors of cathepsin S induction or transcription which satisfy the definition of an inhibitor of cathepsin S as used herein. Nonetheless, upon the discovery of such repressors, their use in the methods and products of the present invention may be highly preferred over currently known inhibitors, and would be regarded as an equivalent embodiment of the disclosed methods and products.

Antisense sequences to cathepsin S may readily be chosen and produced by one of ordinary skill in the art on the basis of the known nucleic acid sequence of the cathepsin S gene (see; e.g., GenBank Accession Nos. M86553, M90696, S39127; and Wiedersranders et at., *J. Biol. Chem.* 267; 13708-13713 (1992)) and the developing field of antisense technology. In order to be sufficiently selective and potent for cathepsin S inhibition, such cathepsin S-antisense oligonucleotides should comprise at least 10 bases and, more preferably, at least 15 bases. Most preferably, the antisense oligonucleotides comprise 18-20 bases. Although oligonucleotides may be chosen which are antisense to any region of the cathepsin S gene or mRNA transcript, in preferred embodiments the antisense oligonucleotides correspond to the N-terminal or translation initiation region of the cathepsin S mRNA, or to mRNA splicing sites. In addition, cathepsin S antisense may, preferably, be targeted to sites in which mRNA secondary structure is not expected (see, e.g., Sainio et al. (1994) *Cell. Mol. Neurobiol.* 14(5):439-457) and at which proteins are not expected to bind.

As will be obvious to one of ordinary skill in the art, the cathepsin S-inhibiting antisense oligonucleotides of the present invention need not be perfectly complementary to the cathepsin S gene or mRNA transcript in order to be effective. Rather, some degree of mismatches will be acceptable if the antisense oligonucleotide is of sufficient length. In all cases, however, the oligonucleotides should have sufficient length and complementarity so as to selectively hybridize to a cathepsin S transcript under physiological conditions. Preferably, of course, mismatches are absent or minimal. In addition, although it is not recommended, the cathepsin S-antisense oligonucleotides may have one or more non-complementary sequences of bases inserted into an otherwise complementary cathepsin S-antisense oligonucleotide sequence. Such non-complementary sequences may loop out of a duplex formed by a cathepsin S transcript and the bases flanking the non-complementary region. Therefore, the entire oligonucleotide may retain an inhibitory effect despite an apparently low percentage of complementarity.

The cathepsin S-antisense oligonucleotides of the invention may be composed of deoxyribonucleotides, ribonucleotides, or any combination thereof. The 5' end of one nucleotide and the 3' end of another nucleotide may be covalently linked, as in natural systems, via a phosphodiester internucleotide linkage. These oligonucleotides may be prepared by art recognized methods such as phosphoramidate, H-phosphonate chemistry, or methylphosphoramidate chemistry (see, e.g., Uhlmann et al. (1990) *Chem. Rev.* 90:543-584; Agrawal (ed.) *Meth. Mol. Biol.*, Humana Press, Totowa, N.J. (1993) Vol. 20; and U.S. Pat. No. 5,149,798) which may be carried out manually or by an automated synthesizer (reviewed in Agrawal et al. (1992) *Trends Biotechnol.* 10:152-158).

The cathepsin S-antisense oligonucleotides of the invention also may include modified oligonucleotides. That is, the oligonucleotides may be modified in a number of ways which do not compromise their ability to hybridize to nucleotide sequences contained within the transcription initiation region or coding region of the cathepsin S gene. The term modified oligonucleotide as used herein describes an oligonucleotide in which at least two of its nucleotides are covalently linked via a synthetic linkage, i.e., a linkage other than a phosphodiester linkage between the 5' end of one nucleotide and the 3' end of another nucleotide. The most preferred synthetic linkages are phosphorothioate linkages. Additional preferred synthetic linkages include alkylphosphonates, phosphorodithioates, phosphate esters, alkylphosphonothioates, phosphoramidates, carbamates, carbonates, phosphate triesters, acetamidate, and carboxymethyl esters. Oligonucleotides with these linkages or other modifications can be prepared according to known methods (see, e.g., Agrawal and Goodchild (1987) *Tetrahedron Lett.* 28:3539-3542; Agrawal et al. (1988) *Proc. Natl. Acad. Sci.* (USA) 85:7079-7083; Uhlmann et al. (1990) *Chem. Rev.* 90:534-583; Agrawal et al. (1992) *Trends Biotechnol.* 10:152-158; Agrawal (ed.) *Meth. Mol. Biol.*, Humana Press, Totowa, N.J. (1993) Vol. 20).

The term modified oligonucleotide also encompasses oligonucleotides with a modified base and/or sugar. For example, modified oligonucleotides include oligonucleotides having the sugars at the most 3' and/or most 5' positions attached to chemical groups other than a hydroxyl group at the 3' position and other than a phosphate group at the 5' position. Other modified ribonucleotide-containing oligonucleotides may include a 2'-O-alkylated ribose group such as a 2'-O-methylated ribose, or oligonucleotides with arabinose instead of ribose. In addition, unoxidized or partially oxidized oligonucleotides having a substitution in one nonbridging oxygen per nucleotide in the molecule are also considered to be modified oligonucleotides.

Such modifications may be at some or all of the internucleoside linkages, at either or both ends of the oligonucleotide, and/or in the interior of the molecule (reviewed in Agrawal et al. (1992) *Trends Biotechnol.* 10:152-158 and Agrawal (ed.)*Meth. Mol. Biol.*, Humana Press, Totowa, N.J. (1993) Vol. 20). Also considered as modified oligonucleotides are oligonucleotides having nuclease resistance-conferring bulky substituents at their 3' and/or 5' end(s) and/or various other structural modifications not found in vivo without human intervention. Other modifications include additions to the internucleoside phosphate linkages, such as cholesteryl or diamine compounds with varying numbers of carbon residues between the amino groups and terminal ribose.

Other non-peptide-based inhibitors of cathepsin S include antibodies, including fragments of antibodies such as Fc, which selectively bind to and inhibit the activity of cathepsin S; and ribozymes which interfere with the transcription, processing or translation of cathepsin S mRNA.

B. Peptide-Based Inhibitors: Generally

Peptide-based inhibitors of cathepsin S are, at the molecular level, mimics or analogs of at least a portion of a natural polypeptide sequence which binds to the active site of cathepsin S as a substrate. In their simplest form, peptide-based inhibitors of cathepsin S are simply peptides which are based upon the sequences adjacent to known cathepsin S cleavage sites. Such peptide-based inhibitors are competitive inhibitors. Preferably, however, peptide-based inhibitors have modified polypeptide structures (whether synthesized from peptides or not) which alter their activity, stability, and/or specificity. The art of combinatorial chemistry has progressed significantly in the design of peptide-based inhibitors such that it is now routine to produce large numbers of inhibitors based on one or a few peptide sequences or sequence motifs (see, e.g. Brömme et al., *Biochem. J.* 315:85-89 (1996), Palmer et al., *J. Med. Chem.* 38:3193-3196 (1995)). Thus, for example, if cathepsin S is known to cleave protein X at position Y, a peptide-based inhibitor of cathepsin S may be chosen or designed as a polypeptide or modified polypeptide having the same sequence as protein X, or structural similarity to the sequence of protein X, in the region adjacent to position Y. In fact, the region adjacent to the cleavage site Y, spanning residues removed by 10 residues or, more preferably, five residues N-terminal and C-terminal of position Y, may be defined as a "preferred protein X cleavage site" for the choice or design of peptide-based inhibitors. Thus, a plurality of peptide-based inhibitors, chosen or designed to span the preferred protein X cleavage site around position Y, may be produced, tested for inhibitory activity, and sequentially modified to optimize or alter activity, stability, and/or specificity.

Preferably, the peptide portion of the peptide-based inhibitors of the invention can be any length, as long the compound can inhibit proteolysis by cathepsin S. Preferably, the peptide portion is about 2 to about 20 amino acids or amino acid equivalents long, more preferably it is about 2 to about 10 amino acids or amino acid equivalents long, and most preferably it is about 2 to about 3 amino acids or amino acid equivalents long.

Modified peptide-based inhibitors of cysteine proteases, as well as other enzymes, are well known in the art. Thus, for example, peptide-based inhibitors of cysteine proteases include peptidyl aldehydes, nitriles, α-ketocarbonyls, halomethyl ketones, diazomethyl ketones, (acyloxy)-methyl ketones, vinyl sulfones, ketomethylsulfonium salts, epoxides, and N-peptidyl-O-acylhydroxylamines (see, e.g., Brömine et al., *Biochem. J.* 315:85-89 (1996); Palmer et al., *J. Med. Chem.* 38(17):3193-3196 (1995); Brömme et al., *Biol. Chem.* 375:343-347 (1994); and references cited therein.

Currently preferred peptide-based inhibitors of cathepsin S include those based upon the sequences Leu-Leu-Leu, and Leu-Hph (where Hph indicates homophenylalanine), as well as the preferred invariant chain cleavage site sequences described below. Thus, for example, morpholinurea-Leu-Hph-vinylsulfone phenyl (LHVS) is one preferred cathepsin S inhibitor. Also preferred are other peptidyl vinyl sulfones, with or without the addition of an N-terminal groups such as carboxybenzyl or nitrophenylacetyl groups, such as Leu-Leu-Leu-vinyl sulfone, N-(carboxybenzyl)-Leu-Leu-Leu-vinylsulfone, and N-(nitrophenylacetyl)-Leu-Leu-Leu-vinylsulfone. Most preferably, the peptidyl moiety corresponds to 2-3 residues chosen from the cathepsin S preferred invariant chain cleavage site, as described below.

C. Peptide-Based Inhibitors: Novel Cathepsin S Inhibitors

As noted above, and evidenced in the Examples below, cathepsin S cleaves the invariant chain, while associated in a class II MHC/invariant chain complex, at two major, nearly adjacent, locations. These major cleavages occur C-terminal of the Arg residue at position 78 or the Lys residue at position 80 of the human invariant chain sequence (SEQ ID NO: 1). See Example 8. Therefore, a preferred invariant chain cleavage site extends around $Arg_{78}$ from N-terminally about positions 68-73 to C-terminally from about positions 83-88. Similarly, a preferred invariant chain cleavage site extends around $Lys_{80}$ from N-terminally about positions 70-75 to C-terminally from about positions 85-90. Because of the overlap of these regions, cathepsin S has a preferred invariant chain cleavage site spanning, approximately, from N-terminally about positions 68-75 to C-terminally about positions 83-90. Thus, peptide-based inhibitors of cathepsin S based upon a sequence of 2-20, more preferably 2-10, and most preferably 2-3 consecutive residues from within this site are provided.

Because of the postulated nature of the cathepsin S active site (see, e.g., Brömine et al., *Biochem. J.* 315:85-89 (1996)), it is particularly preferred that the residues one-, two- and, optionally, three-positions N-terminal to the cleavage sites be included in a peptide based inhibitor. Thus, for example, the residues Asn-Leu (positions 76 and 77; or −2 and −1 relative to the $Arg_{78}$ cleavage point) or the residues Glu-Asn-Leu (positions 75, 76, and 78; or −3, −2 and −1 relative to the $Arg_{78}$ cleavage point) are preferably used as a basis for choosing or designing a peptide-based inhibitor. Similarly, the residues Arg-Met (positions 78 and 79; or −2 and −1 relative to the $Lys_{80}$ cleavage point) or the residues Leu-Arg-Met (positions 77, 78, and 79; or −3, −2 and −1 relative to the $Lys_{80}$ cleavage point) are preferably used as a basis for choosing or designing a peptide-based inhibitor.

Thus, for example, the invention provides novel peptide-based inhibitors such as vinylsulfones compounds including Asn-Leu-vinylsulfone, Arg-Met-vinylsulfone, Leu-Arg-Met-vinylsulfone, Glu-Asn-Leu-vinylsulfone, and Leu-Leu-Leu-vinylsulfone. Modifications of these peptide vinylsulfones are also included in the invention. For example, carboxybenzyl can be present at the N-terminal end to give the following compounds: N-(carboxybenzyl)-Asn-Leu-vinylsulfone, N-(carboxybenzyl)-Arg-Met-vinylsulfone, N-(carboxybenzyl)-Leu-Arg-Met-vinylsulfone, N-(carboxybenzyl)-Glu-Asn-Leu-vinylsulfone, and N-(carboxybenzyl)-Leu-Leu-Leu-vinylsulfone. In an alternative, nitrophenylacetyl is present at the N-terminal end to give the following compounds: N-(nitrophenylacetyl)-Asn-Leu-vinylsulfone, N-(nitrophenylacetyl)-Arg-Met-vinylsulfone, N-(nitrophenylacetyl)-Leu-Arg-Met-vinylsulfone, N-(nitrophenylacetyl)-Glu-Asn-Leu-vinylsulfone, and N-(nitrophenylacetyl)-Leu-Leu-Leu-vinylsulfone. A peptide-based vinylsulfone is meant to include, e.g., a peptide vinylsulfone or a modified peptide vinylsulfone. The invention is also meant to include other modifications of the peptide-based vinylsulfones, e.g., substitutions can be added at the amino terminus of the peptide-based vinylsulfones by, e.g., N-methyl substituents or any other alkyl or substituted alkyl chain, or by substitution with, e.g., phenyl, benzyl, aryl, or modified aryl substituents, as would be known to those skilled in the art.

These examples are merely illustrative and not exhaustive. For example, the peptide-based inhibitors of cathepsin S can be based upon other peptide sequences which span a portion of the preferred invariant chain cleavage site, for example, any 2-3,3-5, 5-7, or more consecutive residues within the preferred invariant chain cleavage site. Similarly, the peptide-based inhibitors may be peptidyl aldehydes, nitriles, α-keto-carbonyls, halomethyl ketones, diazomethyl ketones, (acyloxy)-methyl ketones, vinyl sulfones, ketomethylsulfonium salts, epoxides, N-peptidyl-O-acylhydroxylamines, or other such compounds known to those of skill in the art. Furthermore, the N-termini of these peptide-based inhibitors of cathepsin S may be blocked with a variety of substituent groups, including N-methyl substituents or other alkyl or substituted alkyl chains; phenyl, benzyl, aryl, or modified aryl substituents; or other such substituents known to those of skill in the art.

EXAMPLES

Example 1

Active Site Labeling of Cysteine Proteases

This example illustrates the active site labeling of cysteine proteases, including cathepsin S. The role of cathepsin S in the proteolytic processing of Ii was investigated by exploiting the properties of a number of protease inhibitors, both novel and previously described. The cysteine protease inhibitor Cbz-Tyr-Ala-$CN_2$, irreversibly binds to the active site of cysteine proteases in proportion to their activity. A profile of the active cysteine proteases present within a given cell type can be directly established by incubating the cells with an iodinated form of this inhibitor, Cbz-[$^{125}$I]-Tyr-Ala-$CN_2$ and visualizing the labeled proteases on SDS-PAGE (Mason et al., *Biochem. J.* 257:125-129 (1989)). Cysteine proteases in the cell that are first inactivated with other cysteine class inhibitors prior to incubation with Cbz-[$^{125}$I]-Tyr-Ala-$CN_2$ produce a corresponding decrease in labeling. Inhibition specific for a given protease affects subsequent labeling with Cbz-[$^{125}$I]-Tyr-Ala-$CN_2$ of that specific protease, but not other enzymes present in the preparation.

To examine the cysteine protease profile of professional antigen presenting cells, and measure specifically the activity of cathepsin S, the B-lymphoblastoid cell line HOM2 (Benaroch et at., *EMBO J.* 14:37-49 (1995)) was used. The B-lymphoblastoid cell line HOM2 (homozygous for HLA-DR1) was maintained in RPMI with 10% FBS, 1/1000 units/ml penicillin, 100/μg/ml streptomycin and 2 mM glutamine. HOM2 cells were labeled with Cbz-[[$^{125}$I]-Tyr-Ala-$CN_2$ after incubation with 0.1 nM and 5 nM of the specific cathepsin S inhibitor, LHVS (morpholinurea-leucine-homophenylalanine-vinylsulfone phenyl) (Palmer et al., *J. Med. Chem.* 38(17): 3193-3196 (1995)). Lysates prepared from the labeled cells were analyzed either directly or subjected to immunoprecipitation with antibodies specific for cathepsins S and B by 120% SDS-PAGE. Antibody to human cathepsin S was prepared as described in Shi et al., *J. Biol. Chem.* 269:11530-11536 (1994), and antibody to cathepsin B was obtained from Vital Products, Inc. (St. Louis, Mo.). In the absence of cathepsin S inhibitor, three polypeptides were labeled; migrating at 33 kDa, 28 kDa, and 6 kDa (running with the dye front in this 12% gel). The 33 kDa and 6 kDa polypeptides were immunoprecipitated with an antiserum specific for cathepsin B, and represent 20 the single- and light-chain forms of the active enzyme, respectively. The more intense labeling of the 6 kDa polypeptide compared with the 33 kDa protein suggested that most of the cathepsin B present in HOM2 cells was in the light chain form. The 28 kDa polypeptide was identified as the active form of cathepsin S, as it was immunoprecipitated with an antibody specific for this enzyme. The labeling of cathepsin S, but not cathepsin B, was effectively inhibited at an LHVS concentration of 1 nM. At an inhibitor concentration of 5 nM, the labeling of cathepsin B was decreased, although some activity remained. Thus, LHVS was able to be utilized at 1-5 nM concentrations to specifically inhibit cathepsin S in HOM2 cells, leaving other cysteine proteases functionally active.

The active site labeling of cysteine proteases with Cbz-[$^{125}$I]-Tyr-Ala-$CN_2$ was then used to determine that the purified human cathepsins B and S, used in subsequent experiments were not cross-contaminated with other proteases.

The cysteine protease inhibitor Cbz-Tyr-Ala-CN$_2$ was iodinated as previously reported (Mason et al., *Biochem. J.* 257: 125-129 (1989)). HOM2 cells ($5 \times 10^{-6}$ cells/sample) were incubated with inhibitors 2S,3S-trans-epoxysuccinyl-L-Leu-amido-3-methylbutane ethyl ester (E64D) (20 µm) (obtained from Sigma Chemical Co., St. Louis, Mo.), leupeptin (0.5 mM) (obtained from Sigma Chemical Co., St. Louis, Mo.), concanamycin B (20 nM) (obtained from Ajinomoto Co., Kanagawa, Japan), or LHVS (1 or 5 nM) (obtained from Khepri Pharmaceuticals, Inc., South San Francisco, Calif.) at 37° C. for 1 hour prior to labeling. Cells were labeled by incubation with Cbz-[$^{125}$I]-Tyr-Ala-CN$_2$ for 1 hour at 37° C., washed twice with PBS and lysed in the SDS-PAGE sample buffer. The purified cathepsins B and S were labeled by addition of a 2 µl aliquot of purified enzyme stock to 50 µl of digestion buffer (50 mM Na Acetate, pH 5.5, 1% Triton-X-100, 3 mM cysteine, 1 mM EDTA) containing Cbz-[$^{125}$I-Tyr-Ala-CN$_2$. Samples were incubated for 1 hour at 37° C. and the labeling reaction was stopped by the addition of 50 µl of 2×SDS-PAGE Sample buffer.

Immunoprecipitation of cathepsins B and S was performed by labeling $5 \times 10^6$ HOM2 cells as above followed by cell lysis with 1 ml of 10 mM Tris-HCl, pH 7.5, 1 mM EDTA, 0.2. SIDS, 1% Triton X-100 on ice. Lysates were collected, boiled for 5 minutes and precleared with protein A-agarose (Boehringer Mannheim, Indianapolis, Ind.) plus normal rabbit serum (Sigma Chemical Co., St. Louis, Mo.). The cysteine proteases were immunoprecipitated with anticathepsin S antibody and anti-cathepsin B antibody coupled to protein agarose. The pellets were washed and eluted with reducing SDS-PAGE sample buffer.

Example 2

Inhibition of Cathepsin S Prevents Ii Processing

This example illustrates that inhibition of cathepsin S interferes with processing of Ii and subsequent peptide binding by class II molecules. HOM2 cells were pulsed-labeled with $^{35}$S-methionine/cysteine as follows. HOM2 cells, $5 \times 10^6$/sample, were preincubated in 1 ml methionine-, cysteine-free DMEM supplemented with protease inhibitors or appropriate solvent for 1 hour at 37 C prior to labeling with 0.25 mCi $^{35}$S-methionine/cysteine for 1 hour at 37 C. The cells were centrifuged and resuspended at $1 \times 10^6$/ml in RPMI/10% FBS and chased for 5 hours in the absence or presence of 1 nM or 5 nM LHVS. The HOM2 cells were then washed twice with cold PBS and lysed in 1 ml of 50 mM Tris-HCl, pH 7.4, 0.5% NP-40, 5 mM MgCl$_2$. Lysates were precleared with protein A-agarose. 7 µl of normal rabbit serum and 2 µl of normal mouse serum followed by immunoprecipitation of class II αβ dimers and αβIi complexes with the monoclonal antibody Tu36 coupled to protein A-agarose. Immunoprecipitates were washed 4-6× with 1 ml of 50 mM Tris-HCl, pH 7.4, 0.5% NP-40, 5 mM EDTA, 150 mM NaCl. These pellets were either eluted directly with non-reducing or reducing SDS-PAGE sample buffer, or used as starting material for proteolytic digestion and further immunoprecipitation.

Proteolytic digestion of immunoprecipitates was performed by incubation of precipitated pellets with purified proteases diluted in 50 µl of 50 mM Na Acetate, pH 5.5, 1% Triton X-100, 3 mM cysteine, 1 mM EDTA at 37° C. Samples were eluted with SDS-PAGE sample buffer.

One half of the samples were analyzed by 14% SDS-PAGE under mildly denaturing (nonboiled, nonreduced) conditions to visualize SDS-stable complexes which migrate at approximately 50 kDa. These SDS-stable complexes represent peptide-loaded (αβ-dimers, which decrease upon inhibition of cysteine proteases with leupeptin (Neefjes and Ploegh, *EMBO J.* 11:411-416 (1992)) (obtained from Sigma Chemical Co., St. Louis, Mo.). Specific inhibition of cathepsin S with 1 nM and S nM LHVS resulted in accumulation of a class II-associated 13 kDa Ii fragment, and a concomitant reduction in peptide loading as evidenced by a marked decrease in formation of SDS-stable complexes. Inhibition of all cysteine proteases with the cysteine-class inhibitor 2S,3S-trans-epoxysuccinyl-L-Leu-amido-3-methylbutane ethyl ester (E64D) resulted in a buildup of a class II-associated 23 kDa Ii fragment with a decrease in SDS-stable dimer formation, similar to that seen with leupeptin. This result indicated that cathepsin S acted on a relatively late Ii breakdown intermediate and was required for efficient proteolysis of Ii necessary for subsequent peptide loading.

Example 3

Cathepsin S Selectively Digests Ii Participating in αβIi Complexes

This example illustrates that cathepsin S proteolytically digests the invariant chain in class II MHC/invariant chain complexes, leaving the class II MHC molecule intact and capable of subsequently binding antigenic peptide. Individual α, β, and Ii polypeptides were translated in vitro both separately and together under conditions compatible with complex formation (Bijlmakers et al., *J. Exp. Med.* 180:623-629 (1994)). In vitro translation of α, β and Ii was accomplished as follows: cDNA's of HLA-DRI α (Larhammar et al., *Cell* 30:153-161 (1982)) and P chains (Bell et al., *Proc. Natl. Acad. Sci.* (*USA*) 82:3405-3409 (1985)), and the cDNA encoding the human p33 Ii (Claesson et al., *Proc. Natl. Acad. Sci.* (*USA*) 80:7395-7399 (1983)) were all cloned in pSP72 (Promega, Madison, Wis.) as described previously (Bijlmakers et al., *J. Exp. Med.* 180:623-629 (1994)). The cDNA's were transcribed in vitro either together or separately, using T7 RNA polymerase. RNA was stored in 70% ethanol at −80° C. The optimal amount of RNA utilized was determined empirically for each separate batch of RNA. The resulting RNA's were translated in vitro in rabbit reticulocyte lysate (Flexi, Promega, Madison, Wis.), supplemented with canine microsomes. Translations were performed for 90 minutes at 30° C. as previously described (Bijlmakers et al., *J. Exp. Med.* 180:623-629 (1994)). Upon completion of translation the microsomes, were pelleted by centrifugation for 4 minutes at 12,000 rpm, and resuspended in 20 µl of lysis/digestion buffer (50 mM Na Acetate, pH 5.5, 1% Triton X-100, 3 mM cysteine, 1 mM EDTA) with or without cathepsin S. Cathepsin S concentrations were 0.19 or 0.38 µM. Purified human cathepsin S was obtained by expression in Sf9 cells using the Baculovirus expression system as described (Brömine and McGrath, *Protein Sci.*, in press, 1996). Proteolytic digestion was performed by incubation of the above solubilized microsomes for 4 hours at 37° C. Digestion was stopped by the addition of reducing SDS sample buffer, samples boiled, and analyzed directly by 15% SDS-PAGE under denaturing conditions.

Cathepsin S readily digested the α, β and Ii chains when translated alone. However, when the α and β chains were translated together so that dimer formation occurred, they displayed resistance to proteolysis. When all three moieties were translated together and digested with cathepsin S, only Ii was degraded, illustrating the marked sensitivity of Ii to cathepsin S digestion. The formation of αβ dimers and αβIi trimers were confirmed following each step by immunoprecipitation. Thus, cathepsin S selectively degrades Ii molecules that are part of αβIi complexes, leaving the αβ dimers intact.

To directly compare the ability of cathepsins S and B to degrade Ii participating in αβIi trimers, the activity of the two proteases must be measured, independent of their differences in substrate specificity. Normalization to total protein content is misleading because only a portion of the total protein may be active. To overcome this difficulty, the molar activity of the purified cathepsin B (obtained from Calbiochem-Novabiochem Corp., San Diego, Calif.) and cathepsin S preparations were measured by using E64D (obtained from, Sigma Chemical Co., St. Louis, Mo.) as an active site titrant with the substrate Z-Phe-Arg-AMC, as previously described (Barrett and Kirschke; Methods in Enzymology, Vol. 80, Proteolytic Enzymes, L. Lorand (ed.), New York, N.Y.: Academic Press, Inc., pp 535-560 (1981)). The activities of the enzymes measured in this manner are independent of the substrate used because E64D irreversibly inhibits both cathepsins S and B on an equimolar basis.

Using the concentrations determined by the above method, the ability of cathepsins S and B to digest Ii from αβIi heterotrimers immunoprecipitated from HOM2 cells was determined. HOM2 cells were incubated in the absence of inhibitor, or in the presence of inhibitors E64D or LHVS, during a $^{35}$S-methionine/cysteine pulse/chase. Cathepsin S specifically degraded intact Ii as well as the 23 kDa and 13 kDa Ii intermediates, while sparing the αβ dimer and the αβ-peptide complexes. In contrast, cathepsin B showed little proteolytic activity against immunoprecipitated αβIi trimers or αβIi fragment complexes, even at 100× the molar concentration of cathepsin S. The inability of cathepsin B to digest Ii was not merely a result of the enzyme not being active at the concentrations used, as evidenced by a slight change in migration of the class II β chain, suggesting activity of cathepsin B on the cytoplasmic portion of the P chain (Roche and Cresswell, Proc. Natl. Acad. Sci. (USA) 88:3150-3154 (1991)).

A defined intermediate in the maturation of class II molecules is a complex consisting of the αβ heterodimer bound to the CLIP region of Ii (Avva and Cresswell, Immunity 1:763-774 (1994)). It is this intermediate that was proposed to be a substrate for HLA-DM (see Wolf and Ploegh, Ann. Rev. Cell Biol. 11:267-306 (1995)). To determine if cathepsin S could generate αβ-CLIP from αβIi, HOM2 cells were labeled in the absence and presence of inhibitors, immunoprecipitated with the monoclonal antibody Tu36, digested with 0.23 μM cathepsin S for 1 hour at 37° C., and immunoprecipitated with antibodies directed against Ii. Tu36 is a mouse monoclonal antibody (Shaw et al., Human Immunol. 12:191-211 (1985)) which recognizes HLA-DR1 αβ dimers alone or in association with Ii. Two Ii reactive mouse monoclonal antibodies were used: PIN-1, specific for the N-terminus of Ii (Avva and Cressell, Immunity 1:763-774 (1994)), and the monoclonal antibody LN-2, directed against the C-terminus of Ii. Immunoprecipitates were then boiled for 3 minutes in the presence of 1% SDS to unfold the αβIi complexes, diluted 10-fold and re-immunoprecipitated sequentially with antibodies against the CLIP region, cytoplasmic tail (PIN-1 antibody), and lumenal domain (LN-2 antibody) of Ii. Samples were analyzed by 10-20% gradient tricine SDS-PAGE under denaturing conditions. A 3 kDa polypeptide was immunoprecipitated with the anti-CLIP antibody, which was not found in the undigested samples. The anti-CLIP reagent was generated by injection of rabbits with two overlapping peptides, conjugated to KLH, spanning the region of residues 81-104 of intact human Ii. The antibody directed against the N-terminal cytoplasmic tail, PIN-1, was able to immunoprecipitate intact Ii as well as the 23 kDa and 13 kDa Ii chain fragments, suggesting that both the 23 kDa and 13 kDa intermediates are N-terminal fragments. The LN2 antibody against the Ii lumenal domain precipitated only the full length Ii. Thus, cathepsin S was able to produce αβ-CLIP, a known intermediate in αβIi proteolysis.

In contrast to cathepsin S, neither purified cathepsin B (66 μM) nor D (2.4 μM) (obtained from Calbiochem-Novabiochem Corp., San Diego, Calif.) could produce αβ-CLIP from αβIi. HOM2 cells were pulse/chased in the presence of 0.5 mM leupeptin and class II molecules were immunoprecipitated with Tu36. The isolated class II complexes were then digested with the different purified cathepsins at pH 5.5 for 1 hour at 37° C. The digested complexes were then analyzed by 10-20%, tricine gel under denaturing conditions. Digestion with cathepsin S (0.23 μM) alone resulted in the production of a 3 kDa polypeptide associated with αβ dimers. This 3 kDa fragment could also be re-immunoprecipitated with the anti-CLIP reagent used above. Both cathepsins B and D, when used at high concentrations, could produce large molecular weight Ii cleavage products, but not up-CLIP, illustrating the essential role of cathepsin S in complete and efficient Ii processing.

While inclusion of HLA-DM facilitates exchange of CLIP bound to the αβ-CLIP complex for antigenic peptide (Denzin et al., Cell 82:155-165 (1995); Sherman et al, Immunity 3:197-205 (1995); Sloan et al., Nature 375:802-806 (1995)), the reaction can also occur, albeit less efficiently, in the absence of added HLA-DM. The displacement of larger Ii remnants with antigenic peptides is even less efficient. Proteolysis of αβIi heterotrimers with cathepsin S was shown to allow peptide loading onto the resulting class II αβ-CLIP complexes as follows: HOM2 cells were treated with 20 nM concanamycin B to accumulate a large amount of αβIi trimers (Benaroch et al., EMBO J. 14(1):37-49 (1995)). The hemagglutinin peptide (HA), containing amino acids 306-318, was used as a DR1 restricted peptide (Rothbard et al., Cell 52(4): 515-523 (1988)). HA was synthesized (t-boc chemistry) on a Biosearch SAM 2 peptide synthesizer, dissolved in water and stored at −70° C. The αβIi complexes from concanamycin B treated cells were initially immunoprecipitated with an antibody against the lumenal domain (LN-2) to precipitate only intact αβIi complexes. These complexes were incubated in the absence and presence of 0.23 μM cathepsin S at pH 5.5, and then exposed to $^{125}$I-HA at pH 5.5 for 4 hours. After removal of unbound $^{125}$I-HA, complex formation was assessed by 14% SDS-PAGE under mildly denaturing (non-boiled, nonreduced) conditions. HA peptide was iodinated by incubation of HA (50 μl of 1 mM solution) with $^{125}$I and 50 mM NaPO$_4$ (20 μl), pH 7.5 in an iodogen-coated glass tube on ice for 10 minutes. $^{125}$I-HA was separated from free $^{125}$I by passage over a C18 Sep-pack column, and eluted with acetonitrile. Aliquots of $^{125}$I-HA were dried in a speed-vac and redissolved in digestion buffer for incubation with cathepsin S treated and nontreated immunoprecipitates. Following incubation with the peptide, samples were diluted to 0.8 ml with lysis buffer, pH 7.4, cleared of LN-2 antibody with protein A-agarose and immunoprecipitated with Tu36. Samples were washed thoroughly prior to addition of SDS-PAGE sample buffer to remove unbound peptide.

Digestion of αβIi with cathepsin S and subsequent exposure to $^{125}$I-HA resulted in the formation of labeled αβ-peptide complexes, although this conversion was incomplete as evidenced by the continued presence of SDS-labile class II molecules. Cathepsin S is thus able to process Ii while leaving the class II molecules functionally intact, and shows that cathepsin S is sufficient, by itself, to effectively degrade Ii in a manner that renders αβ-dimers capable of binding peptide.

Example 4

Inhibition of Cathepsin D does not Affect Ii Processing

This example illustrates that neither cathepsin D nor cathepsin H are required for Ii processing. Maric et al., *Proc. Natl. Acad. Sci. (USA)* 91:2171-2175 (1993), have implicated the aspartyl protease cathepsin D in an early step of Ii breakdown. This question was examined by utilizing a potent aspartyl-class protease inhibitor, CGP 53437 (Alteri et al., *Antimic. Ag. Chemotherap.* 37:2087-2092 (1993)) which inhibits cathepsin D in the nanomolar range. CGP 53437 inhibits cathepsin D activity in human monocytes by 75% and 90% at concentrations of 5 μM and 50 μM, respectively. HOM2 cells were labeled with $^{35}$S-methionine/cysteine and chased for 5 hours without inhibitor, in the presence of 0.5 mM leupeptin, 5 nM LHVS, 5 μM CGP 53437 or 50 μM CGP 53437. Samples were analyzed by 14% SDS-PAGE under mildly denaturing conditions. Inhibition of cathepsin D (obtained from Calbiochem-Novabiochem Corp., San Diego, Calif.) with CGP 53437 did not result in accumulation of Ii fragments nor did it produce a decrease in SDS-stable complexes, suggesting that cathepsin D is not essential for Ii processing.

Cathepsin H, a lysosomal cysteine protease with good aminopeptidase but weak endopeptidase activity, is upregulated by γ-interferon in mouse peritoneal macrophages (Lafuse et al., *J. Leuk. Biol.* 57:663-669 (1995)). Purified human cathepsin H (obtained from Calbiochem-Novabiochem Corp., San Diego, Calif.) was not inhibited with LHVS nor did it display any proteolytic activity against immunoprecipitated αβIi, implying that cathepsin H is not an essential protease for Ii degradation.

Example 5

Synthesis of N-(Carboxybenzyl)-Leu-Leu-Leu Vinylsulfone

This example illustrates the steps in the synthesis of carboxybenzyl-Leu-Leu-Leu-vinylsulfone.

a) Weinreb Amide of Boc-Leucine

A dichloromethane solution of Boc-Leucine-H$_2$O (1 equiv.), triethylamine (2 equiv.), and PyBOP (1 equiv.), was stirred for several minutes at room temperature before HCl-N,O-dimethylhydroxylamine (2 equiv.) was added dry, along with additional triethylamine (2 equiv.). After stirring overnight; this reaction mix was diluted with dichloromethane, then washed twice each with 3N HCl, saturated NaHCO$_3$ and saturated NaCl. The dichloromethane phase was dried (over MgSO$_4$) and roto-evaporated, then the product was purified by silica gel flash column chromatography (hexane/ethylacetate, 3:1).

b) Boc-Leucinal

The Weinreb amide of BocLeucine was dissolved in dry Et$_2$O and added by cannula to an Et$_2$O suspension of an equimolar amount of LiAlH$_4$ at 0° C. After stirring for one hour, the reaction flask was removed from 0° C. and allowed to warm to room temperature. After a reaction time of 80 minutes, an aqueous solution of KHSO$_4$, (2 equiv. of KHSO$_4$, 5 ml H$_2$O/mmol of Weinreb amide) was added slowly while stirring. The aqueous phase was extracted with Et$_2$O and the confined Et$_2$O phases were washed with 3N HCl, saturated NaHCO$_3$, and saturated NaCl. After drying (MgSO$_4$,) and rotary evaporation, the oil was found to contain one compound by thin layer chromatography.

c) Phosphonate Sulfone

To a stirring room temperature dioxane solution of diethyl methylthiomethyl phosphonate (1 equiv.) was added 5 equiv. of peracetic acid. After stirring for over 3 hours, Pt on carbon was added to quench unreacted peroxides. The reaction was quenched by the addition of water (10 ml/mmol of the phosphonate sulfide) and the product was extracted with ethylacetate. After drying (MgSO$_4$) and roto-evaporation; the phosphonate sulfone was purified by recrystallization from ethylacetate using a small amount of hexane.

d) Boc-Leu-Vinylsulfone

To a stirring room temperature tetrahydrofuran solution of NaH (2 equiv.) under Argon, was added 2 equiv. of phosphonate sulfone in tetrahydrofuran, by cannula. After stirring for a few minutes, 1 equiv. of Boc-Leucinal in tetrahydrofuran was added by cannula. After 3 hours the reaction was quenched with water and the aqueous phase was extracted with dichloromethane. The combined organic phases were back extracted with saturated NaCl, dried (MgSO$_4$), and roto-evaporated to a yellow oil. The product was purified by flash column chromatography (ethylacetate/hexane, 1:1) to yield an oil after lyophilization.

e) Leu-Vinylsulfone Tosylate Salt

An Et$_2$O solution of anhydrous p-Tosic acid (3 equiv.) was added to dry oil of Boc-Leu-vinylsulfone (1 equiv.) and stirred at room temperature overnight. The product formed a white precipitate which was recovered by centrifugation.

f) Carboxybenzyl-Leu-Leucine

To three volumes of a stirring room temperature H$_2$O/NaHCO$_3$ solution of Leucine (1.5 equiv.) was added one volume of dioxane solution of carboxybenzyl-Leu-Osu (1 equiv.), and was stirred overnight. The product was precipitated by addition of aqueous sodium citrate, and then was extracted by ethylacetate. The combined ethylacetate phases were dried (MgSO$_4$,) and roto-evaporated to a clear oil. The product was purified by flash column chromatography (dichloromethane/MeOH, 12:1, with 1% TFA).

g) Carboxybenzyl-Leu-Leu-Leu-Vinylsulfone

To a stirred tetrahydrofuran solution of carboxybenzyl-Leu-Leucine (1 equiv.), at −10° C., under Argon, was added 1 equiv. each of N-methylmorpholine and isobutyl chloroformate. After a few minutes, a tetrahydrofuran suspension of 1 equiv. each of Leu-vinylsulfone tosylate and N-methylmorpholine, was added and stirring at −10° C. was continued for 75 minutes. The reaction was quenched by the addition of 3N HCl and the product was extracted with dichloromethane. After flash column chromatography (ethylacetate/hexane, 3:2) the product was recrystallized from warm ethanol.

Example 6

Synthesis of Other Peptide-Based Vinylsulfones

This example illustrates the steps in the synthesis of peptide vinylsulfones and modified peptide vinylsulfones.

(i) Asn-Leu-vinylsulfone

This compound is synthesized as described in Example 5 except that in step (g), asparagine is used instead of carboxybenzyl-Leu-leucine.

(ii) Arg-Met-vinylsulfone

This compound is synthesized as described in Example 5 except that in step (g), arginine is used instead of carboxybenzyl-Leu-leucine, and that in step (a) Boc-L-methionine is used and converted to Boc-methional as in (b) and used in steps (d) and (e).

(iii) Leu-Arg-Met-vinylsulfone

This compound is synthesized as described above for compound (ii), except that Leu arginine is used in step (g).

(iv) Glu-Asn-Leu-vinylsulfone

This compound is synthesized as described above for compound (i), except that Glu-asparagine is used in step (g).

(v) N-(carboxybenzyl)-Asn-Leu-vinylsulfone

This compound is synthesized as described above for compound (i), except that carboxybenzyl-protected asparagine is used.

(vi) N-(carboxybenzyl)-Arg-Met-vinylsulfone

This compound is synthesized as described above for compound (ii), except that carboxybenzyl-protected arginine is used.

(vii) N-(carboxybenzyl)-Leu-Arg-Met-vinylsulfone

This compound is synthesized as described above for compound (iii), except that carboxybenzyl-protected Leu arginine is used.

(viii) N-(carboxybenzyl)-Glu-Asn-Leu-vinylsulfone

This compound is synthesized as described above for compound (iv), except that carboxybenzyl-protected Glu-asparagine is used.

(ix) N-(nitrophenylacetyl)-Asn-Leu-vinylsulfone

This compound is synthesized as described above for compound (v), except that nitrophenylacetyl-protected asparagine is used.

(x) N-(nitrophenylacetyl-Arg-Met-vinylsulfone

This compound is synthesized as described above for compound (vi), except that nitrophenylacetyl-protected arginine is used.

(xi) N-(nitrophenylacetyl-Leu-Arg-Met-vinylsulfone

This compound is synthesized as described above for compound (vii), except that nitrophenylacetyl-protected Leu-arginine is used.

(xii) N-nitrophenylacetyl)-Glu-Asn-Leu-vinylsulfone

This compound is synthesized as described above for compound (viii), except that nitrophenylacetyl-protected Glu-asparagine is used.

Example 7

Inhibition of Cathepsin S Alters Immune Response

This example illustrates that inhibition of cathepsin S altered the immune response to tetanus toxoid. Peripheral blood mononuclear cells (PBMC's) were isolated from a tetanus immune individual and cultured in the presence of tetanus toxoid (250 ng/cc), cysteine-class protease inhibitor E64D (20 µM) (obtained from Sigma Chemical Co., St. Louis, Mo.) and specific cathepsin S inhibitor LHVS (morpholinurea-leucine-homophenylalanine-vinylsulfone phenyl) (10-20 nM) obtained from Khepri Pharmaceuticals, Inc., South San Francisco, Calif.) for 3-5 days. T cell proliferation was assayed by $^3$H-thymidine uptake during the final 18 hours of culture. In the presence of tetanus toxoid (obtained from Sigma Chemical Co., St. Louis, Mo.), $^3$H-thymidine uptake increased more than four-fold. Both E64D and LHVS attenuated this response by approximately 60%. Thus, specific inhibition of cathepsin S modulated an immune response. The fact that the attenuation of T cell stimulation was of the same magnitude as that produced by complete inhibition of all cysteine proteases supports the conclusion that cathepsin S is the major cysteine protease involved in invariant chain processing and subsequent antigen presentation.

Example 8

Specific Invariant Chain Cleavage Sites for Cathepsin S

This example illustrates the specific cleavage sites for cathepsin S at the N-terminus of CLIP. HOM2 cells (Benaroch et al., *EMBO J.* 14:37-49 (1995)) were pulse/chased with 5 mCi $^{35}$S-methionine for 5 hours in the presence of 20 mM E64D, lysed, and class II MHC molecules immunoprecipitated with mAb Tu36. The immunoprecipitates were digested with 0.23 µM cathepsin S for 60 minutes at 37° C., pH 5.5. Class II MHC molecules were repelleted, analyzed on a 10-20% tricine gel and transferred to nylon membrane. A radioactive band migrating at 3 kDa was excised from the membrane and subjected to radiosequencing. A high level of counts was found in the first cycle corresponding to the methionine at invariant chain residue 79. A smaller increase in counts was also evident at cycle 11 indicating that a proportion of the peptides present had an N-terminus at the leucine residue 81. Thus, bipeptide and tripeptide-vinylsulfones spanning these cleavage sites are excellent candidates for inhibition of cathepsin S-mediated invariant chain processing in vivo.

Example 9

Treating Multiple Sclerosis with Leu-Arg-Met-Vinylsulfone

This example illustrates a method for treating multiple sclerosis in a human with a peptide-based vinylsulfone which inhibits proteolysis of the invariant chain by cathepsin S. The patient is given Leu-Arg-Met-vinylsulfone by injection intravenously, once a day. The dose is 500 mg/70 kg body weight. This treatment alleviates the effects of multiple sclerosis in the patient.

Example 10

Treating Pemphigus Vulgaris with N-(Carboxybenzyl)-Arg-Met-Vinylsulfone

This example illustrates a method for treating pemphigus vulgaris in a human with a peptide-based vinylsulfone which inhibits proteolysis of the invariant chain by cathepsin S. N-(carboxybenzyl)-Arg-Met-vinylsulfone is topically applied in the form of an ointment to the lesions resulting from the disease. The dose is 50 mg/gm of ointment and is applied daily to the affected area. This treatment alleviates the effects of pemphigus vulgaris in the patient.

Those skilled in the art will be able to ascertain, using no more than routine experimentation, many equivalents of the specific embodiments of the invention described herein. These and all other equivalents are intended to be encompassed by the following claims.

What is claimed is:

1. A method for suppressing pain associated with a class II MHC-restricted immune response in a mammal, comprising administering to said mammal an effective amount of an agent which inhibits cathepsin S, wherein said agent is a peptide-based inhibitor of cathepsin S.

2. The method of claim 1, wherein said effective amount of said agent inhibits proteolysis of invariant chain by cathepsin S and thereby inhibits formation of class II/antigenic peptide complexes from class II MHC/invariant chain complexes in said mammal.

3. A method for suppressing pain in a mammal by inhibiting invariant chain proteolysis from class II MHC/invariant chain complexes, comprising administering to said mammal an agent which inhibits cathepsin S, wherein said agent is a peptide-based inhibitor of cathepsin S.

4. A method as in claim 1, wherein said agent is a selective inhibitor of cathepsin S relative to a cysteine protease selected from cathepsins K, L, H and B.

5. A method as in claim 1, wherein said agent is a specific inhibitor of cathepsin S.

6. A method as in claim 1, wherein said peptide-based inhibitor of cathepsin S is based upon a peptide sequence which comprises 2-20 consecutive residues of a preferred invariant chain cleavage site of cathepsin S.

7. A method as in claim 6, wherein said peptide-based inhibitor is based upon a peptide sequence selected from Asn-Leu, Glu-Asn-Leu, Arg-Met, Leu-Arg-Met, Leu-Leu-Leu, and Leu-Hph.

8. The method of claim 1, wherein the agent is administered to the mammal via intravenous injection, intradermal injection, subcutaneous injection. intramuscular injection, intraperitoneal injection, anal supposition, vaginal supposition, oral ingestion or inhalation.

9. The method of claim 1, wherein administration of the agent to the mammal comprises repeated administration of the agent to the mammal.

10. The method of claim 1, wherein said peptide-based inhibitor is morpholinurea-leucine-homophenyl alanine-vinylsulfone phenyl (LHVS).

11. The method of claim 1, wherein said peptide-based inhibitor is a peptide-based vinylsulfone or a modified peptide-based vinylsulfone.

12. The method of claim 1, wherein said peptide-based inhibitor is selected from peptidyl aldehydes, nitriles, α-ketocarbonyls, halomethyl ketones, diazomethyl ketones, (acyloxy)-methyl ketones, vinyl sulfones, ketomethylsulfonium salts, epoxides, and N-peptidyl-O-acyl-hydroxylamines.

13. The method of claim 1, wherein said agent is selected from Asn-Leu-vinylsulfone, Arg-Met-vinylsulfone, Leu-Arg-Met-vinylsulfone, Glu-Asn-Leu-vinylsulfone, and Leu-Leu-Leu-vinylsulfone.

14. The method of claim 1, wherein said agent is selected from N-(carboxybenzyl)-Asn-Leu-vinylsulfone, N-(carboxybenzyl)-Arg-Met-vinylsulfone, N-(carboxybenzyl)-Leu-Arg-Met-vinylsulfone, N-(carboxybenzyl)-Glu-Asn-Leu-vinylsulfone, and N-(carboxybenzyl)-Leu-Leu-Leu-vinylsulfone.

15. The method of claim 1, wherein the agent is agent is a selective inhibitor of cathepsin S relative to cathepsin B.

16. The method of claim 1, wherein the agent is agent is a selective inhibitor of cathepsin S relative to cathepsin L.

17. The method of claim 1, wherein the agent has at least two-fold selectivity for cathepsin S relative to a cysteine protease selected from cathepsins K, L, H and B.

* * * * *

UNITED STATES PATENT AND TRADEMARK OFFICE
CERTIFICATE OF CORRECTION

PATENT NO. : 7,427,591 B2
APPLICATION NO. : 10/913045
DATED : September 23, 2008
INVENTOR(S) : Ploegh et al.

Page 1 of 1

It is certified that error appears in the above-identified patent and that said Letters Patent is hereby corrected as shown below:

Please insert the following in the specification of U.S. Patent No. 7,427,591 at column 1, line 3:

-- Sponsorship Information
This invention was made with government support under Grant Number R01 AI038577 awarded by the National Institutes of Health. The government has certain rights in this invention. --

Signed and Sealed this
Thirteenth Day of March, 2012

David J. Kappos
*Director of the United States Patent and Trademark Office*

```
                              SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
          (A) LENGTH: 217 amino acids
          (B) TYPE: amino acid
          (C) STRANDEDNESS: <Unknown>
          (D) TOPOLOGY: linear (ii) MOLECULE TYPE: protein (ix) FEATURE:
          (A) NAME/KEY: Protein
          (B) LOCATION: 1..217
          (D) OTHER INFORMATION: /note= "Invariant chain protein"

(xi) SEQUENCE DESCRIPTION: SEQ ID NO: 1:

Met Asp Asp Gln Arg Asp Leu Ile Ser Asn Asn Glu Gln Leu Pro Me
1               5                   10                  15

Leu Gly Arg Arg Pro Gly Ala Pro Glu Ser Lys Cys Ser Arg Gly Al
            20                  25                  30

Leu Tyr Thr Gly Phe Ser Ile Leu Val Thr Leu Leu Leu Ala Gly Gl
        35                  40                  45

Ala Thr Thr Ala Tyr Phe Leu Tyr Gln Gln Gln Gly Arg Leu Asp Ly
    50                  55                  60

Leu Thr Val Thr Ser Gln Asn Leu Gln Leu Glu Asn Leu Arg Met Ly
65                  70                  75                  80

Leu Pro Lys Pro Pro Lys Pro Val Ser Lys Met Arg Met Ala Thr Pr
                85                  90                  95

Leu Leu Met Gln Ala Leu Pro Met Gly Ala Leu Pro Gln Gly Pro Me
            100                 105                 110

Gln Asn Ala Thr Lys Tyr Gly Asn Met Thr Glu Asp His Val Met Hi
        115                 120                 125

Leu Leu Gln Asn Ala Asp Pro Leu Lys Val Tyr Pro Pro Leu Lys Gl
    130                 135                 140

Ser Phe Pro Glu Asn Leu Arg His Leu Lys Asn Thr Met Glu Thr Il
145                 150                 155                 160

Asp Trp Lys Val Phe Glu Ser Trp Met His His Trp Leu Leu Phe Gl
                165                 170                 175

Arg Met Ser Arg His Ser Leu Glu Gln Lys Pro Thr Asp Ala Pro Pr
            180                 185                 190

Lys Glu Ser Leu Glu Leu Glu Asp Pro Ser Ser Gly Leu Gly Val Th
        195                 200                 205

Lys Gln Asp Leu Gly Pro Val Pro Met
    210                 215
```